United States Patent
Walker

[11] Patent Number: 5,944,179
[45] Date of Patent: Aug. 31, 1999

[54] PROTECTIVE SHEATH FOR MEDICAL PROBE

[76] Inventor: Diana G. Walker, 5664 Bailey Grant Rd., Jeffersonville, Ind. 47130

[21] Appl. No.: 09/084,487

[22] Filed: May 26, 1998

[51] Int. Cl.⁶ .......................... B65D 85/38; B65D 81/16
[52] U.S. Cl. .......................... 206/305; 206/363; 206/523
[58] Field of Search ................... 206/305, 306, 206/363, 368, 438, 523

[56] References Cited

U.S. PATENT DOCUMENTS

| | | | |
|---|---|---|---|
| 921,149 | 5/1909 | Norwood | 206/305 |
| 1,786,271 | 12/1930 | Stonebraker | 206/306 |
| 3,027,286 | 3/1962 | Kurhan | 206/523 X |
| 3,308,940 | 3/1967 | Morris, Jr. | 206/306 |
| 3,309,893 | 3/1967 | Heffler et al. | 206/523 X |
| 3,360,760 | 12/1967 | Johnson | 206/523 X |
| 3,373,863 | 3/1968 | Afton | 206/306 |
| 4,349,031 | 9/1982 | Perlin . | |
| 4,385,692 | 5/1983 | Eldridge, Jr. | 206/363 |
| 4,524,868 | 6/1985 | Buckley et al. | 206/523 X |
| 4,911,559 | 3/1990 | Meyst et al. . | |
| 4,912,989 | 4/1990 | Cassidy | 374/140 X |
| 5,088,834 | 2/1992 | Howe et al. . | |
| 5,188,459 | 2/1993 | Mino et al. . | |
| 5,667,068 | 9/1997 | Weaver | 206/363 |

*Primary Examiner*—Bryon P. Gehman
*Attorney, Agent, or Firm*—Maurice L. Miller, Jr.

[57] ABSTRACT

A physical shock absorbing sheath for the protection of the fragile piezoelectric quartz crystal tip of an ultrasonic probe, such as is used for medical and veterinary purposes, is disclosed. The sheath includes an elongated body which is preferably in the form of a right circular cylinder or rectangular parallelepiped. A hollow shaft is formed longitudinally through a portion of the body and opens onto an upper end thereof for insertion of the fragile tip and shaft portion of the probe therein, preferably as the probe hangs by a flexible cord from a wall hanger or wall hook. A lower end of the body is supported in its operative position on a table or work bench located below the hanger. Fracture of the delicate probe tip and other impact damage due to the probe being knocked about or failing from its hanger while in a stored condition between uses on patients is thus substantially prevented. The sheath can be constructed of compressible foam material such as low density polyethylene or, more preferably, a breathable foam material such as open cell polyurethane.

15 Claims, 1 Drawing Sheet

PROTECTIVE SHEATH FOR MEDICAL PROBE

BACKGROUND OF THE INVENTION

This invention relates generally to a physical shock absorbing sheath or cover for protecting a fragile tip and/or shaft of a medical or veterinary probe while in storage, especially an ultrasonic probe which employs a delicate piezoelectric quartz crystal tip.

Medical probes, such as endovaginal and rectal probes of the ultrasonic type, contain a delicate crystal tip which can easily be fractured or otherwise damaged and rendered useless, as when dropped on a hard surface or as knocked about while hanging from a wall hanger in storage ready for use in a hospital lab. Occasionally these probes are accidentally knocked loose from their wall hanger, whereupon they fall onto the surface of an underlying table, work bench or floor. In any case, damage to the crystal tip of such a probe can not be repaired, by reason of which the entire probe must be discarded and replaced. Such probes are quite expensive and, in a busy hospital where many such probes are used, the loss of such probes due to accidental impact damage is often a major expense, particularly when accumulated over the course of an entire accounting year.

Broadly speaking, special purpose covers for various types of medical instruments have been known and used in the prior art. See, for example, U.S. Pat. No. 4,349,031 issued to A. R. Perlin on Sept. 14, 1982; U.S. Pat. No. 4,911,559 issued to R. P. Meyst et al. On Mar. 27, 1990; U.S. Pat. No. 5,088,834 issued to R. R. Howe et al. On Feb. 18, 1992; and U.S. Pat. No. 5,188,459 issued to K. Mino on Feb. 23, 1993. The Perlin device is a disposable esophageal probe cover which covers a probe while inserted into a patient's mouth, which cover is removed after the probe is withdrawn and replaced with a clean cover prior to use of the probe on the next patient. The Meyst et al. cover includes three laminated layers for covering a thermometer while in use and is adapted so as to interfere only minimally with temperature detection of the thermometer sensor. The Howe et al. device is a sheath of infrared transparent material for use with an infrared type thermometer for the purpose of providing a sanitary barrier between the instrument and the patient on which it is used. The Mino et al. device is also a disposable protective shield, in this case for a radiation type thermometer for use in measuring the temperature of a glossy metal surface. The reference shield is said to protect the glossy surface from damage which might otherwise occur due to direct contact with the unshielded thermometer.

None of these prior art devices are seen as offering protection of the instrument or of a fragile portion thereof from impact damage while being held in a stored condition prior to use.

By means of my invention, this and other problems encountered with the handling, transporting and storage of medical and veterinary probes, especially those of a delicate nature having a fragile tip or other portion, are substantially overcome.

SUMMARY OF THE INVENTION

It is an object of my invention to provide a protective sheath for a medical or veterinary probe for protecting said probe from damage due to physical impact while in a stored but ready to use condition.

It is a further object of my invention to provide a relatively inexpensive disposable protective sheath for a medical or veterinary probe.

It is another object of my invention to provide a protective sheath for a medical or veterinary probe which is constructed of a breathable foam material to aid in drying the probe while in a stored, ready to use condition following sterilization thereof.

It is yet another object of my invention to provide a protective sheath for a conventional ultrasonic probe of the type which includes a piezoelectric quartz crystal tip, the sheath thus protecting the tip from fracture due to physical impact.

Briefly, in accordance with my invention, a protective sheath for a medical or veterinary probe is provided. The sheath includes an elongated body of compressible material defining a hollow, longitudinally extending blind shaft therein which opens onto one end thereof. The hollow shaft is sized to accommodate a distal end portion of a medical veterinary probe therein for protecting the tip of the probe from damage due to physical impact.

These and other objects, features and advantages of the present invention will become apparent to those skilled in the art from the following detailed description and attached drawings upon which, by way of example, only a preferred and one other important embodiment of my invention is explained and illustrated.

DESCRIPTION OF THE PREFERRED EMBODIMENT

Figure 1:
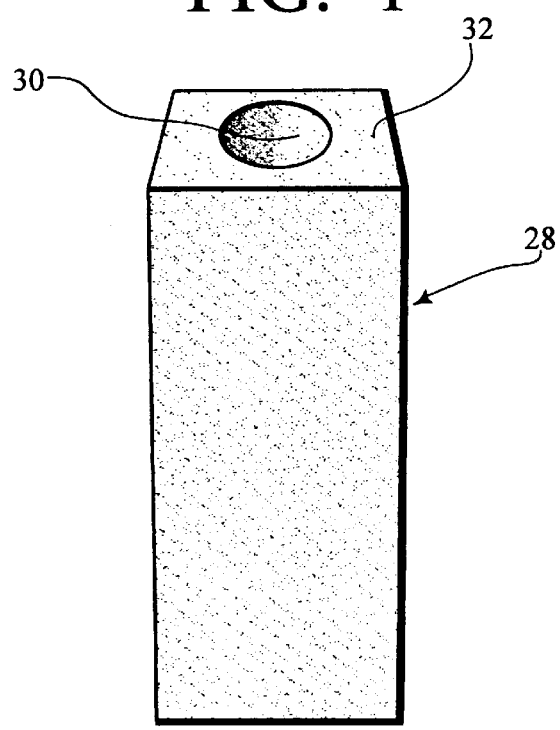
FIG. 1 shows a perspective view of a protective sheath for a medical or veterinary instrument, thus illustrating a preferred embodiment of my invention.
Figure 2:
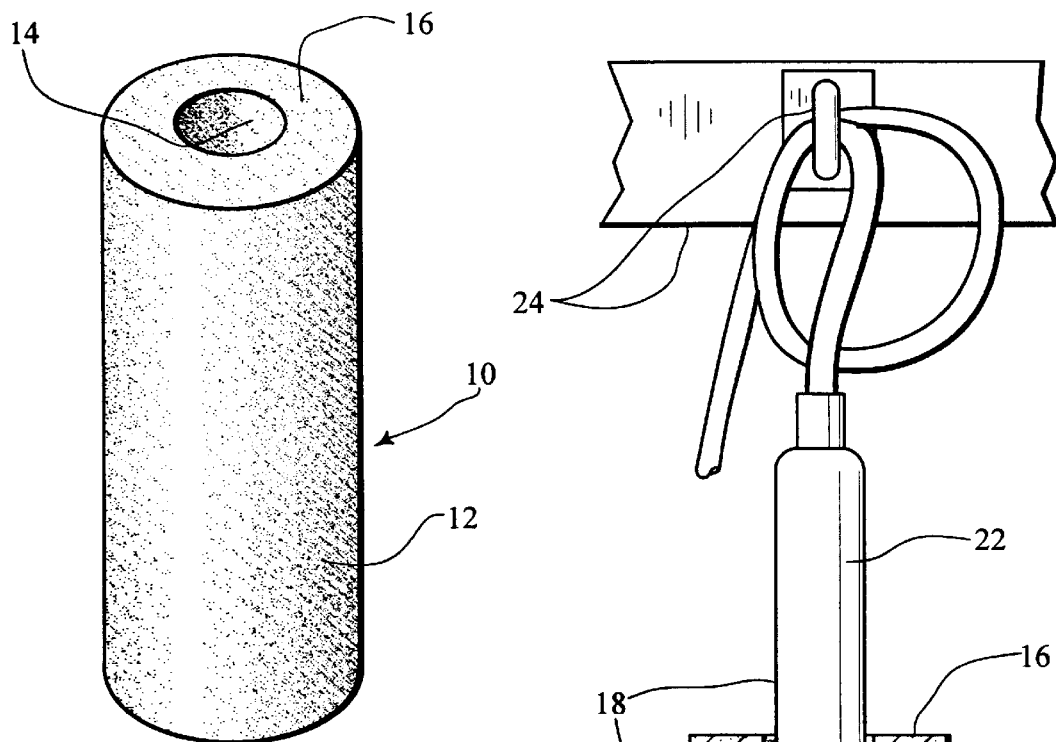
FIG. 2 shows a cross sectional elevation view of the sheath of FIG.1 and a conventional ultrasonic probe suspended from a wall hook and having a distal end portion inserted and protectively cushioned in the sheath.

Referring now to the drawing figures and, in particular to FIGS. 1–2 there is shown, in a preferred embodiment of my invention, a cover or protective sheath, generally designated 10, for a medical or veterinary probe which includes an elongated body 12. The body 12 is preferably constructed in the shape of an elongated, right circular cylinder, although other shapes are within the scope of my invention as later exemplified. A hollow blind shaft 14 which, preferably, is also cylindrically shaped extends longitudinally and coaxially through a portion of the body 12 and opens on an upper end 16 thereof.

As shown in FIG. 2, the sheath 10 is adapted to protect a medical probe, such as, for example, an ultrasonic probe 18 having a piezoelectric quartz crystal tip 19 from impact damage, whereby the hollow shaft 14 should be preferably of sufficient size, i.e. diameter and length, to accommodate a distal end portion or shaft portion 20 of the probe below a handled portion 22. The terms "distal" and "distal end portion" as used herein refer to the point of view of the operator of the probe 18 and not to that of the patient or animal upon which the probe is used. Ultrasonic probes, such as the probe 18 include endovaginal and rectal probes, among other types, and have a tendency to have their delicate quartz crystal tip 19 fractured or otherwise damaged when dropped or when knocked off of a wall hanger or wall hook 24, from which they are frequently suspended, onto a hard surface, such as a table or work bench 26. Probes, such as the probe 18, are quite expensive and, when the tip 19 is fractured or otherwise damaged, the entire instrument must be discarded and replaced.

While I have constructed the sheath 10 from a low density, compressible, polyethylene foam material, which provides excellent cushioning for the probe tip 19 and shaft 20 from physical shock or impact, I prefer to use a breathable material such as, for example, an open cell polyurethane foam. Such breathable material permits volatile and nonvolatile liquid vapor residues on the surface of the tip 19 and shaft 20, resulting from sterilization of the probe 18, to escape through the wall of the sheath 10, as well as upwardly through the shaft 14 around the probe 18, to ambient atmosphere to aid in drying the probe after being placed on the hanger 24 and inserted into the blind shaft 14 for storage prior to use on a next patient. Because of the relative low cost of the sheath 10 of my invention when made of a compressible foam material, the sheath can be discarded after a single use with the probe 18 for probe storage purposes between uses of the probe on successive patients. When using polyethylene foam material, I have found it suitable to provide a sheath, such as the sheath 10 which is cut from readily available cylindrically shaped stock having a three inch diameter. I cut the cylindrical stock to a length of eight inches and drill a hollow cylindrically shaped shaft, such as at 14, coaxially and longitudinally through one end thereof to a depth of about six inches. The resulting blind shaft 14 should preferably have a diameter of about 1¼ inches. These dimensions of the sheath 10 and hollow blind shaft 14 provide sufficient wall thickness about the shaft and depth of solid material before the base of the shaft to adequately cushion and, otherwise, protect the probe tip 19 and shaft 20 from impact damage while the probe is stored therein between uses. Of course, these suggested dimensions are illustrative only and may be varied substantially as desired or required as, for example, where probes of different sizes are to be protected.

Figure 3:
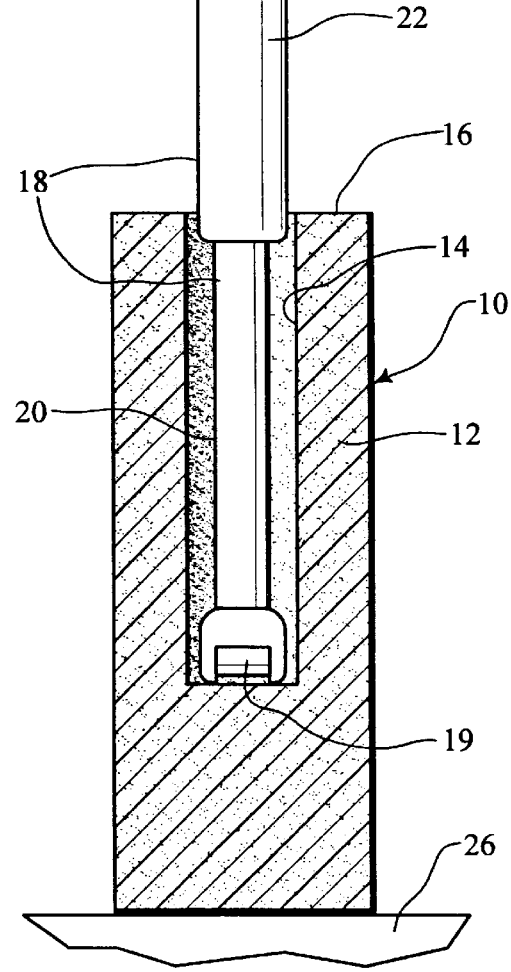
FIG. 3 shows a perspective view of an alternative protective sheath for a medical instrument, thus illustrating another important embodiment of my invention.

Referring now to FIG. 3, another embodiment of my invention is shown which comprises an elongated sheath 28 of suitable molded foam material, such as previously described, which is constructed in the form of a rectangular parallelepiped. As in the previous example, a blind shaft 30 is formed which extends longitudinally partially through the center of the sheath from an access opening of an upper end 32 thereof. The sheath 28 is usable to confine and protect the shaft and tip of a medical or veterinary probe in the same manner as the sheath 10 of the previous example, such as, for example, where the probe is suspended by its cord from a wall hanger, the same as shown in FIG. 2 of the previous example.

While the right circular cylindrical shape of the sheath 10 is preferred, since it can be cut and drilled from readily available foam stock, it will be appreciated that, as in the case of the sheath 28 of FIG. 3, the sheath of my invention can take on any of numerous other solid geometric shapes as desired. Also, it will be understood that the hollow blind shaft, as shown at 14 in FIGS. 1–2 and at 30 in FIG. 3, need not be limited to a cylindrical shape but could have a molded rectangular cross-section or other suitable geometric shape as desired.

Although the present invention has been described and illustrated with respect to certain specific details of certain preferred and otherwise important embodiments of my invention, it is not intended that such details limit the scope or coverage of this patent other than as specifically set forth in the following claims.

I claim:

1. A protective sheath for a medical or veterinary probe comprising an elongated body of compressible material defining a hollow longitudinally extending, blind shaft which opens onto one end of said body and which is sized for insertion of a distal end portion of such a probe therein for protecting a tip and a distal end portion of a medical or veterinary probe from damage due to physical impact, and a medical or veterinary probe having a tip and a shaft portion, said tip and at least a distal end portion of said shaft portion being inserted in said blind shaft.

2. The sheath of claim 1 wherein said material comprises a polymer foam.

3. The sheath of claim 1 wherein said material comprises a low density polyethylene foam.

4. The sheath of claim 1 wherein said material is breathable to permit liquid vapor to escape from said probe through the hollow shaft defining wall of said material to ambient atmosphere.

5. The sheath of claim 4 wherein said breathable material comprises an open cell foam.

6. The sheath of claim 5 wherein said foam is open cell polyurethane.

7. The sheath of claim 1 wherein said elongated body is cylindrically shaped.

8. The sheath of claim 1 wherein said body is cylindrically shaped and said hollow blind shaft is cylindrically shaped.

9. The sheath of claim 1 wherein said body is shaped in the form of a rectangular parallelepiped.

10. The sheath of claim 1 wherein said body is of unitary construction.

11. The sheath of claim 1 wherein said probe comprises an ultrasonic instrument.

12. In combination with a medical or veterinary probe which includes a fragile tip, a shaft portion and a handled portion, a protective sheath comprising an elongated body of compressible material defining a hollow, longitudinally extending, blind shaft in said body which opens onto one end of said body and which is sized for insertion of a distal end portion of a shaft portion of a medical or veterinary probe therein for protecting the tip and shaft portion of said probe from damage due to physical impact, said tip and at least a majority portion of the length of said shaft portion being inserted in said blind shaft.

13. The combination of claim 12 wherein said blind shaft is sized for insertion of said tip and substantially the entire length of said shaft portion therein, substantially the entire length of said shaft portion being inserted in said blind shaft.

14. The combination of claim 12 wherein said material comprises a polymer foam, said body being of unitary construction.

15. The combination of claim 12 wherein said probe comprises an ultrasonic instrument.

* * * * *